(12) United States Patent
Petzoldt et al.

(10) Patent No.: US 7,122,707 B2
(45) Date of Patent: Oct. 17, 2006

(54) METHOD FOR PRODUCING AN ANNULAR SHELL CATALYST AND USE THEREOF FOR PRODUCING ACROLEIN

(75) Inventors: Jochen Petzoldt, Mannheim (DE); Signe Unverricht, Mannheim (DE); Heiko Arnold, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 480 days.

(21) Appl. No.: 10/398,287

(22) PCT Filed: Oct. 9, 2001

(86) PCT No.: PCT/EP01/11643

§ 371 (c)(1),
(2), (4) Date: Apr. 10, 2003

(87) PCT Pub. No.: WO02/30569

PCT Pub. Date: Apr. 18, 2002

(65) Prior Publication Data

US 2003/0187305 A1 Oct. 2, 2003

(30) Foreign Application Priority Data

Oct. 10, 2000 (DE) .............................. 100 49 873
Dec. 1, 2000 (DE) .............................. 100 59 713

(51) Int. Cl.
C07C 45/00 (2006.01)
B01J 31/00 (2006.01)
B01J 23/00 (2006.01)
B01J 21/00 (2006.01)

(52) U.S. Cl. ............ 568/479; 568/477; 502/104; 502/113; 502/255; 502/308; 502/311; 502/316; 502/317; 502/322; 502/323

(58) Field of Classification Search ............... 502/104, 502/113, 249, 254, 305, 308, 311, 321, 322, 502/323, 349, 353–355, 415, 407, 439, 255, 502/316, 317; 568/477, 479
See application file for complete search history.

(56) References Cited

U.S. PATENT DOCUMENTS

| 3,936,505 | A | * | 2/1976 | Oda et al. .................... 502/215 |
|---|---|---|---|---|
| 4,035,418 | A | * | 7/1977 | Okada et al. ............... 562/538 |
| 4,111,984 | A | * | 9/1978 | Ishii et al. .................... 562/538 |
| 4,259,211 | A | * | 3/1981 | Krabetz et al. ............. 502/178 |
| 4,358,622 | A | * | 11/1982 | Nemec et al. ............... 568/470 |
| 5,191,116 | A | * | 3/1993 | Yamamatsu et al. ........ 562/549 |
| 5,210,293 | A | * | 5/1993 | Kitson ..................... 562/512.2 |
| 5,281,745 | A | * | 1/1994 | Ushikubo et al. ........... 558/319 |
| 5,449,821 | A | * | 9/1995 | Neumann et al. ........... 562/546 |
| 6,043,185 | A | * | 3/2000 | Cirjak et al. ................. 502/311 |
| 6,143,921 | A | * | 11/2000 | Karim et al. ................ 560/245 |
| 6,171,571 | B1 | * | 1/2001 | Bedard et al. ........... 423/594.7 |
| 6,428,765 | B1 | * | 8/2002 | Bedard et al. ........... 423/594.8 |
| 6,737,545 | B1 | * | 5/2004 | Hibst et al. .................. 562/535 |

FOREIGN PATENT DOCUMENTS

DE 29 09 671 10/1980

(Continued)

Primary Examiner—Cam N. Nguyen
(74) Attorney, Agent, or Firm—Oblon, Spivak, McClelland, Maier & Neustadt, P.C.

(57) ABSTRACT

Coated catalysts which are suitable for the gas-phase catalytic oxidation of propene to acrolein are prepared by a process in which rings are used as supports and water is used as a binder.

16 Claims, 1 Drawing Sheet

FOREIGN PATENT DOCUMENTS

Figure 1:
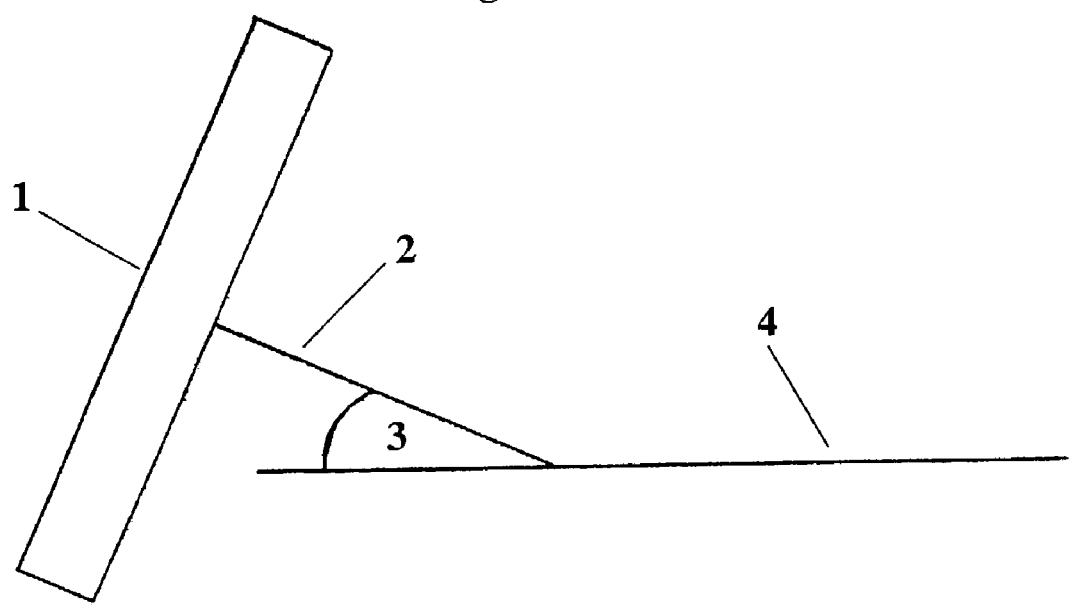

| | | |
|---|---|---|
| DE | 40 23 239 | 1/1992 |
| DE | 44 31 957 | 3/1995 |
| DE | 44 42 346 | 5/1996 |
| DE | 196 55 913 | 6/2000 |
| DE | 199 48 523 | 4/2001 |
| EP | 0 900 774 | 3/1999 |
| WO | 95/26820 | 10/1995 |
| WO | 00 53557 | 9/2000 |

* cited by examiner

METHOD FOR PRODUCING AN ANNULAR SHELL CATALYST AND USE THEREOF FOR PRODUCING ACROLEIN

BACKGROUND OF THE INVENTION

Field of the Invention

The present invention relates to a process for the preparation of a catalyst which consists of a support and a catalytically active oxide material applied to the surface of the support and of the formula I $$Mo_{12}Bi_aX^1{}_bFe_cX^2{}_dX^3{}_eO_y \qquad (I),$$

where
$X^1$ is Co and/or Ni,
$X^2$ is Si and/or Al,
$X^3$ is Li, Na, K, Cs and/or Rb,
$0.2 \leq a \leq 1$,
$2 \leq b \leq 10$,
$0.5 \leq c \leq 10$,
$0 \leq d \leq 10$,
$0 \leq e \leq 0.5$ and
y is a number which is determined assuming charge neutrality as a result of the valency and frequency of the elements other than oxygen in I, in which a thorough dry blend is produced from starting compounds of the elemental constituents of the catalytically active oxide material, the thorough dry blend is subjected to a thermal treatment at from 150 to 350° C. to give a precursor material, the support is moistened with water, a layer of the precursor material is caused to adhere to the surface of the moistened support by bringing the latter into contact with finely divided precursor material, the coated support is then dried and finally the dried support coated with precursor material is calcined at from 400 to 600° C.

The present invention furthermore relates to catalysts which are obtainable by the above process and their use for the gas-phase catalytic oxidation of propene to acrolein.

DESCRIPTION OF THE BACKGROUND

The preparation of the important intermediate acrolein by heterogeneously catalyzed gas-phase oxidation of propene is generally known (cf. for example DE-A 19855913).

Acrolein is used, inter alia, for the preparation of acrylic acid, whose alkyl esters are used in particular as monomers for the preparation of aqueous polymer dispersions.

It is also known that multimetal oxide materials of the formula I can be used as catalytically active oxide materials for catalysts for the heterogeneously catalyzed gas-phase oxidation of propene to acrolein.

For example, DE-A 19855913 recommends the use of rings formed exclusively from active multimetal oxides I (unsupported catalyst rings) and the use of active multimetal oxides I applied to spherical supports (spherical coated catalysts) as catalysts for the gas-phase catalytic oxidative preparation of acrolein from propene.

However, the disadvantage of the procedure recommended in DE-A 19855913 is that, on the one hand, the mechanical stability of the unsupported catalyst rings and, on the other hand, the selectivity and activity of the acrolein formation in the case of the spherical coated catalysts are not completely satisfactory. The same applies to the spherical coated catalysts of WO 95/26820.

DE-A 4442346 relates to the preparation of annular coated catalysts comprising active multimetal oxide materials of the formula I. DE-A 4442346 recommends the use of a solution which consists of from 20 to 90% by weight of water and from 10 to 80% by weight of an organic compound dissolved in water as a liquid binder for applying the active multimetal oxides I. The disadvantage of the annular coated catalysts of DE-A 4442346 is that their activity and selectivity with respect to the acrolein formation are also unsatisfactory during use as catalysts for the gas-phase catalytic partial oxidation of propene.

EP-A 900774 likewise describes the preparation of coated catalysts whose active material stoichiometry corresponds to the formula I.

According to the description of EP-A 900774, the geometry of the support used for the preparation of the coated catalysts may be arbitrary. Furthermore, according to the description of EP-A 900774 suitable liquid binders are those of a very wide range of types (including water). In the examples of EP-A 900774, exclusively spherical supports are used and the binder used is always an aqueous glycerol solution.

Although the coated catalysts prepared in EP-A 900774 are recommended as catalysts for the gas-phase catalytic oxidation of propene to acrolein, they are satisfactory neither with respect to their activity nor with respect to the selectivity of the acrolein formation.

In the prior application DE-A 19948523, annular coated catalysts are likewise recommended for the gas-phase catalytic oxidation of propene to acrylic acid, but DE-A 19948523 does not describe any specific processes for their preparation.

SUMMARY OF THE INVENTION

It is an object of the present invention to provide a process for the preparation of a catalyst consisting of a support and a catalytically active oxide material applied to the surface of the support, which process gives coated catalysts which are suitable as coated catalysts having improved activity and higher selectivity with respect to the acrolein formation for the gas-phase catalytic oxidation of propene to acrolein.

We have found that this object is achieved by a process for the preparation of a catalyst which consists of a support and a catalytically active oxide material applied to the surface of the support and of the formula I $$Mo_{12}Bi_aX^1{}_bFe_cX^2{}_dX^3{}_eO_y \qquad (I),$$

where
$X^1$ is Co and/or Ni,
$X^2$ is Si and/or Al,
$X^3$ is Li, Na, K, Cs and/or Rb,
$0.2 \leq a \leq 1$,
$2 \leq b \leq 10$,
$0.5 \leq c \leq 10$,
$0 \leq d \leq 10$,
$0 \leq e \leq 0.5$ and
y is a number which is determined assuming charge neutrality as a result of the valency and frequency of the elements other than oxygen in I, in which a thorough dry blend is produced from starting compounds of the elemental constituents of the catalytically active oxide material, the thorough dry blend is subjected to a thermal treatment at from 150 to 350° C., preferably from 220 to 280° C., to give a precursor material, the support is moistened with water, a layer of the precursor material is caused to adhere to the surface of the moistened support by bringing the latter into contact with finely divided precursor material, the coated support is then dried and finally the dried support coated with precursor material is calcined at from 400 to 600° C., wherein the support has annular geometry.

DETAILED DESCRIPTION OF THE PREFERRED EMBODIMENTS

The annular supports to be used according to the invention are preferably chemically inert, i.e. they exhibit substantially no participation in the course of the catalytic gas-phase oxidation of propene to acrolein, which is catalyzed by the coated catalysts prepared according to the invention. According to the invention, particularly suitable materials for the supports are alumina, silica, silicates, such as clay, kaolin, steatite, pumice, aluminum silicate and magnesium silicate, silicon carbide, zirconium dioxide and thorium dioxide.

The surface of the support may be either smooth or rough. Advantageously, the surface of the support is rough since greater surface roughness generally results in a higher adhesive strength of the applied coat of catalyst precursor material or of oxidic active material. Frequently, the surface roughness $R_z$ of the support is from 40 to 200 µm, often from 40 to 100 µm (determined according to DIN 4768 Sheet 1 using a Hommel tester for DIN-ISO surface parameters, from Hommelwerke, Del.).

Furthermore, the support material may be porous or nonporous. Expediently, the support material is nonporous (total volume of the pores, based on the volume of the support, $\leq 1\%$ by volume).

The length of the support rings to be used according to the invention is typically from 2 to 10 mm and their external diameter is typically from 4 to 10 mm. The wall thickness of the support rings is usually from 1 to 4 mm. The support ring dimensions suitable according to the invention are also from 3 to 6 mm (length), from 4 to 8 mm (external diameter) and from 1 to 2 mm (wall thickness). Of course, from 2 to 4 mm (length), from 4 to 8 mm (external diameter) and from 1 to 2 mm (wall thickness) are also suitable as annular geometry according to the invention.

Support ring geometries notable according to the invention are, for example, 7 mm×3 mm×1.5 mm (external diameter×length×wall thickness) and 5 mm×3 mm×1.5 mm (external diameter×length×wall thickness).

The thickness of the active oxide material present on the coated catalysts obtainable according to the invention is as a rule from 10 to 1000 µm. However, it may also be from 100 to 700 µm, from 200 to 600 µm or from 300 to 500 µm. Possible coat thicknesses are also from 10 to 500 µm or from 200 to 300 µm.

The fineness of the precursor material to be applied to the surface of the annular support is of course adapted to the desired thickness of the active oxide material coat. For a coat thickness of from 100 to 500 µm, for example, powders comprising precursor material of which at least 50% of the powder particles pass through a sieve of mesh size from 1 to 10 µm and whose proportion of particles having a maximum dimension above 50 µm is less than 1% (based on the total number of particles) are suitable. As a rule, the distribution of the maximum dimensions of the powder particles corresponds to a Gaussian distribution, as a result of the preparation.

In order to achieve the desired coat thickness, it is expedient to repeat the novel process periodically. This means that the support provided with a base coat subsequently forms, in a manner according to the invention, supports first to be moistened and then to be coated by contact with dry finely divided precursor material, etc. The addition of finely divided precursor material and of binder is effected as a rule continuously.

For carrying out, on an industrial scale, the coating process to be used according to the invention, it is therefore advisable to use, for example, the basic procedure disclosed in DE-A 2909671.

This means that the supports to be coated are expediently initially taken in an inclined rotating container (e.g. rotating plate or coating drum or coating pan) (the angle of inclination (angle of the central axis of the rotating container relative to the horizontal; cf. FIG. 1, in which 1=coating drum (side view), 2=central axis of drum, 3=angle of inclination, 4=horizontal) is $\geq 0°$ and $\leq 90°$, as a rule $\geq 30°$ and $\leq 90°$).

The rotating container conveys the support under two metering apparatuses arranged at a specific interval in succession. The first of the two metering apparatuses expediently corresponds to a nozzle (for example an atomizer nozzle operated with compressed air), through which the supports rolling in the rotating plate are sprayed with water and are moistened in a controlled manner. The second metering apparatus is located outside the atomization cone of the water sprayed in as a binder and serves for feeding in the finely divided precursor material (for example via a vibrating channel or powder screw). The support rings moistened in a controlled manner take up the precursor material powder fed in, which, as a result of the rotational movement, becomes compacted on the outer surface of the annular supports to give a cohesive coat (such a compacting movement does not take place in the inner circle of the hollow cylindrical support, which is why this remains substantially uncoated).

If required, the support provided with a base coat in this manner once again passes through the spray nozzle in the course of the subsequent revolution, is moistened thereby in a controlled manner to be able to receive a further layer of finely divided precursor material in the course of the further movement, etc. (intermediate drying is generally not necessary).

The removal of the binder to be used according to the invention as water can be effected, for example, by supplying heat, for example by the action of hot gases, such as $N_2$ or air. Of course, the drying can also be effected in a drying oven. The drying temperature is as a rule from 100 to 150° C.

It is noteworthy that the novel process results in both satisfactory adhesion of successive coats to one another and of the base coat to the surface of the support.

What is important for the described form of the novel process is that the moistening of the support surface to be coated is carried out in a controlled manner. In brief, this means that the support surface is expediently moistened in such a way that it contains absorbed-water, but no liquid phase as such is visible on the support surface. If the support surface is too moist, the particles of the finely divided precursor material combine to form separate agglomerates instead of coating the surface. Detailed information in this context is to be found in DE-A 2909671.

An advantage of the novel process is that the removal of the water used as a binder can be effected in a controlled manner, for example by evaporation. In a simple case, this can be effected by the action of hot gases of corresponding temperature (usually from 100 to 150° C.). However, only preliminary drying can be achieved by the action of hot gases. The final drying can then be effected, for example, in any desired drying oven (for example a belt dryer).

An important feature of the novel process is that it is not the catalytically active oxidic material as such but a precursor material which is applied to the support.

The annular support coated with the precursor material and dried must, according to the invention, be calcined for producing the catalytically active oxidic material. This can be effected within a period of a few hours (typical calcination times are from 2 to 10 hours, the required calcination time decreasing with increasing calcination temperature) at from 400 to 600° C., preferably from 430 to 500° C.

The calcination can be carried out under an oxidizing, inert or reducing atmosphere. Expediently, it is effected under air. Of course, it can also be carried out under reduced pressure. For example, inert gases such as molecular nitrogen and/or noble gases, such as He and Ar, are suitable for producing an inert gas atmosphere. The calcination can be carried out, for example, in a through-circulation oven.

For the preparation of the catalyst precursor material with which the annular supports are to be coated according to the invention, it is usual to start from those sources of the constituents of the catalytically active, oxidic material which are suitable in a manner known per se and to produce from these a very thorough, as a rule finely divided, dry blend, which is then subjected to a thermal treatment at from 150 to 350° C., preferably from 220 to 280° C. (as a rule for from 1 to 6 hours). This thermal treatment can also be carried out under an inert, reducing or oxidizing atmosphere. Usually, it is carried out under air. The precursor material formed during the thermal treatment, under which the sources used generally decompose, can then be applied in finely divided form to the support rings.

What is important is that the sources to be used according to the invention are either oxides or those compounds which can be converted into oxides by heating, at least in the presence of oxygen. In addition to the oxides, particularly suitable starting compounds are therefore ammonium metallates, halides, nitrates, formates, oxalates, acetates, carbonates or hydroxides.

The thorough mixing of the starting compounds can be effected in dry or in wet form. If it is effected in dry form, the starting compounds are expediently used as finely divided powder and are subjected to thermal treatment according to the invention after mixing and, if required, molding.

Preferably, however, the thorough mixing is effected in wet form. Usually, the starting compounds are mixed with one another in the form of an aqueous solution or suspension. The aqueous material is then dried. The drying is advantageously carried out by spray-drying (the gas inlet temperature is as a rule from 280 to 420° C. and the gas outlet temperature is typically from 100 to 150° C.). The powder obtained in the spray-drying frequently proves to be too finely divided for further processing directly. In these cases, it can be kneaded with the addition of water. After the kneading, the kneading material is expediently divided into coarse particles and dried (for example at from 100 to 150° C. in a drying oven). The drying can then be followed by the thermal treatment at from 150 to 350° C., required according to the invention, before the precursor material obtained is converted, for example by milling, into the required finely divided form for the novel coating purpose.

Coated catalysts preferred according to the invention are those whose catalytically active oxide material comprises only Co as $X^1$. $X^2$ is preferably Si and $X^3$ is preferably K, Na and/or Cs, particularly preferably K.

The stoichiometric coefficient a is advantageously $0.4 \leq a \leq 1$, particularly preferably $0.4 \leq a \leq 0.95$. The stoichiometric coefficient b is preferably $4 \leq b \leq 8$, particularly preferably $6 \leq b \leq 8$. The value for the variable c is advantageously $1 \leq c \leq 5$, particularly advantageously $2 \leq c \leq 4$. The stoichiometric coefficient e is expediently >0. Preferably, $0.01 \leq e \leq 0.5$, particularly preferably $0.05 \leq e \leq 0.2$.

The value for the stoichiometric coefficient of oxygen, y, is obtained from the valency and frequency of the cations, assuming charge neutrality. Novel coated catalysts having catalytically active oxide materials whose Co/Ni molar ratio is at least 2:1, preferably at least 3:1, particularly preferably at least 4:1, are advantageous. Most preferably, only Co is present.

In particularly preferred novel coated catalysts, the value for $1.5 \times (a+c)+b$ is $\geq 11$ and $\leq 14$, preferably $\geq 11.5$ and $\leq 13$. Values for $1.5 \times (a+c)+b$ of $\geq 11.8$ and $\leq 12.5$ are particularly preferred.

Furthermore, those novel coated catalysts whose catalytically active oxide material corresponds to a catalytically active oxide material specified in DE-A 19855913 are suitable according to the invention.

The coated catalysts obtainable according to the invention are suitable not only for selective gas-phase oxidation of propene to acrolein but also for the partial gas-phase oxidation of other organic compounds (other alkenes, alkanes, alkanones or alkenols) to α,β-unsaturated aldehydes and/or carboxylic acids. The preparation of acrylic acid from acrolein and the preparation of methacrolein and methacrylic acid from isobutene, isobutane, tert-butanol or tert-butyl methyl ether may be mentioned by way of example.

The general reaction conditions to be maintained for the use of the novel coated catalysts for the gas-phase catalytic oxidation of propene to acrolein are described, for example, in DE-A 4023239 and in DE-A 4431957.

The novel coated catalysts are especially suitable for carrying out the partial gas-phase oxidation of propene to acrolein using high propene loadings of the catalyst load, as described, for example, in DE-A 19955168, in DE-A 19948523 and in DE-A 19948248. An important feature is that they have high activity and high selectivity of the acrolein formation even at high propene loading.

Finally, it should be noted that the coated catalysts obtainable according to the invention and consumed in a gas-phase catalytic oxidation of propene to acrolein can be regenerated as described in EP-A 339119.

EXAMPLES AND COMPARATIVE EXAMPLES

A) Preparation of a Precursor Material a Having the Stoichiometry $Mo_{12}Bi_{0.6}Fe_3Co_7Si_{1.6}K_{0.08}O_x$ Solution A:

1252.51 g of iron(III) nitrate (14.2% by weight of Fe) were added to 3530.05 g of an aqueous cobalt(II) nitrate solution (12.4% by weight of Co) heated to 60° C., via a powder funnel while stirring in the course of one minute while maintaining the 60° C. After the end of the addition, stirring was continued for a further 30 minutes at 60° C. Finally, 1198.99 g of an aqueous bismuth nitrate solution (11.1% by weight of Bi) were stirred in via a dropping funnel in the course of two minutes while maintaining the 60° C. After stirring for a further ten minutes at 60° C., a clear, red aqueous solution A was obtained.

Solution B:

10.18 g of an aqueous KOH solution (46.8% by weight of KOH) were stirred into 2500 g of water. The solution was then heated to 60° C. while stirring. Thereafter, 2249.72 g of ammonium heptamolybdate were added in portions while stirring and while maintaining the 60° C., and stirring was continued for a further hour at 60° C. A slightly turbid pale yellow aqueous solution B was obtained.

Precipitation:

The aqueous solution A at 60° C. was added to the aqueous solution B at 60° C. by means of a pump while stirring in the course of 15 minutes. After the end of the addition, stirring was continued for a further 5 minutes at 60° C. Thereafter, 204.11 g of silica sol (Ludox®TM, Du Pont, 50% by weight of $SiO_2$, density: 1.39 g/ml, pH: 8.8, alkali metal content ≦0.5% by weight) were added while stirring, and stirring was continued for a further five minutes at 60° C.

Spray-Drying:

The aqueous mixture obtained was spray-dried in a spray dryer from Niro (Niro A/S Atomizer Transportable Minor spray dryer, centrifugal atomizer from Niro, DK). The temperature of the initially taken material was 60° C. The gas inlet temperature was 360±10° C. and the gas outlet temperature was 115±5° C.

The total aqueous mixture was sprayed cocurrently with a delivery of 2 l/h via a binary nozzle with a dashed atomizer wheel with an initial spray nozzle pressure of 5.2 bar with air as carrier gas (40 $m^3$/h). After the powder deposition in a cyclone, a spray powder having a particle size of from 20 to 25 μm was obtained.

Kneading:

400 g of the spray-dried powder were kneaded in a type LUK 075 1 l kneader from Werner & Pfleiderer with the addition of 150 ml of water. The kneader had two sigma blades operated in opposite directions. The kneading was effected in three steps, which lasted for 5, 10 and 15 minutes. Before the third kneading step, the material being kneaded was broken up by hand, thoroughly mixed and removed from the kneading blades in order to ensure uniform mixing.

Drying:

After the kneading, the kneaded material was broken up into coarse particles and dried for 2 hours in a type FD 53 drying oven from Binder, Del. (53 l internal volume) at 120° C.

Decomposition:

The dried kneaded material was subjected to a thermal treatment in a type N60/A through-circulation oven (60 l internal volume) from Nabertherm, Del. The oven was first heated to 240° C. in the course of 2 hours and was kept at this temperature for 10 minutes. It was then heated to 280° C. in the course of 60 minutes. This temperature was kept constant for one hour. During the entire process, a gas stream of 300 l (S.T.P)/l of air was passed through the through-circulation oven. A precursor material A was thus obtained.

B) Preparation of a Precursor Material B Having the Stoichiometry B $Mo_{12}Bi_{0.2}Fe_{4.0}Co_7Si_{1.6}K_{0.08}O_x$ Solution A':

1678.22 g of iron(III) nitrate (14.2% by weight of Fe) were added to 3547.38 g of a cobalt(II) nitrate solution (12.4% by weight of Co) heated to 60° C., via a powder funnel in the course of one minute while stirring and while maintaining the 60° C. After the end of the addition stirring was continued for a further 30 minutes at 60° C. Finally, 401.63 g of an aqueous bismuth nitrate solution (11.1% by weight of Bi) were added in the course of 2 minutes via a dropping funnel and while stirring at 60° C. Stirring was then continued for a further 10 minutes at 60° C. A clear red solution A' was obtained.

Solution B':

10.23 g of an aqueous KOH solution (46.8% by weight of KOH) was stirred into 2500 g of water. The aqueous solution was heated to 60° C. while stirring. 2260.76 g of ammonium heptamolybdate were then added in portions while maintaining the 60° C. and while stirring. Thereafter, stirring was continued for a further hour at 60° C., and a slightly turbid pale yellow solution B' was thus obtained.

Precipitation:

The solution A' at 60° C. was added to the initially taken, aqueous solution B' at 60° C. in the course of 15 minutes while stirring by means of a pump. After the end of the addition, stirring was continued for a further 5 minutes at 60° C. Thereafter, 205.11 g of silica sol (Ludox®TM, Du Pont, 50% by weight of $SiO_2$, density: 1.39 g/ml, pH: 8.8, alkali metal content ≦0.5% by weight) were added while maintaining the 60° C., and stirring was continued for a further 5 minutes at 60° C.

Spray-drying, kneading, drying and decomposition were then carried out as under A), and a precursor material B was thus obtained.

C) Preparation of Novel Coated Catalysts and Comparative Coated Catalysts

General Preparation Features:

The precursor material to be used for coating was milled in a centrifugal mill (type ZM 100, from Retsch, Del.) to a particle size >0 and ≦0.12 mm. Specifically, the particle size distribution is as follows:

| D(μm) | 1 | 1.5 | 2 | 3 | 4 | 6 | 8 | 12 | 16 |
|---|---|---|---|---|---|---|---|---|---|
| x | 80.5 | 76.3 | 67.1 | 53.4 | 41.6 | 31.7 | 23 | 13.1 | 10.8 |
| y | 19.5 | 23.7 | 32.9 | 46.6 | 58.4 | 68.3 | 77 | 86.9 | 89.2 |

| D(μm) | 24 | 32 | 48 | 64 | 96 | 128 |
|---|---|---|---|---|---|---|
| x | 7.7 | 4 | 2.1 | 2 | 0 | 0 |
| y | 92.3 | 96 | 97.9 | 98 | 100 | 100 |

The meanings are as follows:
D = diameter of the particle.
X = percentage of particles whose diameter is ≧ D.
Y = percentage of particles whose diameter is < D.

124 g of the milled precursor material were applied to 250 g of support ($R_z$=45 μm, carrier material=steatite, total pore volume of the support ≦1% by volume (based on total volume of support)). For this purpose, the support was initially taken in a coating drum (2 l internal volume, angle of inclination of the central axis of the drum relative to the horizontal=30°). The drum was rotated at 25 revolutions per minute. About 45 ml of liquid binder were sprayed onto the support in the course of 60 minutes via an atomizer nozzle operated with compressed air. The nozzle was installed in such a way that the spray cone wetted the supports transported in the drum by the driver plates at the uppermost point of the inclined drum, in the upper half of the rolling zone. The finely divided precursor material was introduced into the drum via a powder screw, the point of powder addition being within the rolling addition zone but below the spray cone. By periodic repetition of wetting and powder metering, the support provided with a base coat itself became the support in the subsequent period. After the end of the coating, the coated support was dried for 2 hours at 120° C. in a drying oven (from Binder, Del., internal volume 53 l). The dried coated catalyst precursors were then calcined in a through-circulation oven from Heraeus, Del. (type K 750/2 S, internal volume 55 l) through which 800 l (S.T.P.)/h of air flowed.

For this purpose, the through-circulation oven was heated linearly in the course of 210 minutes from 25° C. to 470° C. This temperature was then maintained for 6 hours. The coated catalysts prepared in this manner had a coat of active material which was 370±30 μm thick in all cases.

| | |
|---|---|
| Comparative coated catalyst CCC1: | The precursor material A was used, spheres with a diameter of from 2.5 to 3.5 mm were used as supports, and the liquid binder was water; |
| Novel coated catalyst NCC1: | As for CCC1, but hollow cylinders having an external diameter of 7 mm, a length of 3 mm and an internal diameter of 4 mm-were used as supports; |
| Comparative coated catalyst CCC2: | As for NCC1, but a 25% strength by weight solution of glycerol in water was used as the liquid binder; |
| Comparative coated catalyst CCC3: | As for NCC1 but, instead of the precursor material A, a precursor material A calcined for 6 hours at 470° C. in the abovementioned through-circulation oven (through which 800 l (S.T.P.)/h of air flowed) from Heraeus was used for the coating (the through-circulation oven was heated in the course of 210 minutes from 25° C. to 470° C. by linear temperature increase) . The calcination after the coating of the supports and drying was omitted. |
| Comparative coated catalyst CCC4: | As for CCC1, but the precursor material B was used; |
| Novel coated catalyst NCC2: | As for NCC1, but the precursor material B was used; |
| Comparative coated catalyst CCC5: | As for CCC2, but the precursor-material B was used. |

D) Testing of the Coated Catalysts Prepared Under C

A reaction tube comprising V2A stainless steel (external diameter=21 mm, internal diameter=15 mm) was loaded in each case with the coated catalysts. The loading length in all cases was chosen so that the fixed catalyst bed contained from 32 to 34 g of active material.

The reaction tube was heated over its entire length by means of a salt bath flowing around it. The reaction gas starting mixture used was a mixture of 5% by volume of propene, 9.5% by volume of oxygen and 85.5% by volume of nitrogen. The loading of the reaction tube with reaction gas starting mixture was 100 l (S.T.P.)/h in all cases. The salt bath temperature was set in all cases so that a propene conversion C of 95 mol % was achieved in a single pass through the reaction tube.

In the product gas stream, the selectivity S of the formation of the desired product acrolein was determined by gas chromatographic analysis.

C and S are defined as follows:

$$C(\text{mol }\%) = \frac{\text{Number of moles of propene in the starting mixture} - \text{number of moles of propene in the product mixture}}{\text{Number of moles of propene in the starting mixture}} \times 100$$

-continued $$S(\text{mol }\%) = \frac{\text{Number of moles of acrolein in the product mixture}}{\text{Number of moles of propene in the starting mixture} - \text{number of moles of propene in the product mixture}} \times 100$$

The table below shows the salt bath temperatures $T_s[°C.]$ required with the different coated catalysts (the lower the required salt bath temperature, the higher the catalyst activity) and the resulting selectivities of the acrolein formation and the exact conversions of propene. The selectivity data are relative selectivity data $S_R$, i.e. within the series of coated catalysts CCC1, NCC1, CCC2 and CCC3, the selectivity of the acrolein formation achieved with CCC1 was set equal to 100 and the selectivity of the acrolein formation achieved with the other three coated catalysts was related thereto.

In a corresponding manner, within the series of coated catalysts CCC4, NCC2 and CCC5, the selectivity of the acrolein formation achieved with CCC4 was set equal to 100.

TABLE

| Coated catalyst | $T_s[°C.]$ | C[mol-%] | $S_R$ |
|---|---|---|---|
| CCC1 | 363 | 94.9 | 100 |
| NCC1 | 335 | 95.2 | 102.3 |
| CCC2 | 347 | 94.2 | 101.9 |
| CCC3 | 370 | 94.8 | 98.7 |
| CCC4 | 359 | 95.0 | 100 |
| NCC2 | 334 | 95.1 | 102.1 |
| CCC5 | 345 | 94.9 | 100.4 |

We claim:

1. A process for the preparation of a catalyst, which consists of a support having annular geometry and a catalytically active oxide material having formula I applied to the surface of the support $$Mo_{12}Bi_aX^1{}_bFe_cX^2{}_dX^3{}_eO_y \qquad (I),$$

wherein
  $X^1$ is Co and/or Ni,
  $X^2$ is Si and/or Al,
  $X^3$ is Li, Na, K, Cs and/or Rb
  $0.2 \leq a \leq 1$,
  $2 \leq b \leq 10$,
  $0.5 \leq c \leq 10$,
  $0 \leq d \leq 10$,
  $0 \leq e \leq 0.5$ and
  y is a number which is determined assuming charge neutrality as a result of the valency and frequency of the elements other than oxygen in formula I, wherein the process comprises:
  (a) preparing a thorough dry blend from starting compounds of the elemental constituents of the catalytically active oxide material,
  (b) thermally treating the thorough dry blend at a temperature ranging from 150 to 350° C. to give a finely divided precursor material,
  (c) moistening the support having annular geometry with water,
  (d) adhering a layer of the finely divided precursor material to the surface of the moistened support by bringing the latter into contact with the finely divided precursor material, thereby having obtained a coated catalyst, (e) drying the coated support, and (f) finally calcining the dried support coated with precursor material at a temperature ranging from 400 to 600° C.

2. The process as claimed in claim 1, wherein the support consists of alumina, silica, clay, kaolin, steatite, pumice, aluminum silicate, magnesium silicate, silicon carbide, zirconium dioxide or thorium dioxide.

3. The process as claimed in claim 1, wherein the surface roughness $R_z$ of the support ranges from 40 to 200 mm.

4. The process as claimed in any of claim 1, wherein the total volume of the pores of the support is $\leq 1\%$ by volume, based on the volume of the support.

5. The process as claimed in any of claim 1, wherein the support is comprised of individual components that have a annular geometry of a length ranging from 2 to 10 mm, an external diameter ranging from 4 to 10 mm and a wall thickness ranging from 1 to 4 mm.

6. The process as claimed in claim 5, wherein the support is comprised of individual components that have an annular geometry of a length ranging from 3 to 6 mm, an external diameter ranging from 4 to 8 mm and a wall thickness ranging from 1 to 2 mm.

7. The process as claimed in claim 5, wherein the support is comprised of individual components that have an annular geometry of a length ranging from 2 to 4 mm, an external diameter ranging from 4 to 8 mm and a wall thickness ranging from 1 to 2 mm.

8. The process as claimed in claim 1, wherein the coating thickness of the catalytically active oxide material applied to the surface of the support ranges from 10 to 1000 mm.

9. The process as claimed in claim 8, wherein the coating thickness of the catalytically active oxide material applied to the surface of the support ranges from 100 to 500 mm.

10. The process as claimed in claim 1, wherein the steps of moistening a support material having been provided with a base coat and then contacting the moistened surface of the support material with finely divided precursor material are repeatedly performed in a periodic manner.

11. The process as claimed in claim 10, wherein the support to be coated is introduced into a rotating container which transports the support periodically under two metering apparatuses arranged in succession, the first of which moistens the support rolling in the rotating container by spraying with water and the second of which meters in the precursor material in finely divided form.

12. The process as claimed in claim 1, wherein $X^1$ is Co.

13. The process as claimed in claim 1, wherein $X^2$ is Si.

14. The process as claimed in claim 1, wherein $X^3$ is K.

15. A catalyst prepared by a process as claimed in claim 1.

16. A process for the gas-phase catalytic oxidation of propene to acrolein in the presence of the catalyst as claimed in claim 15.

* * * * *